(12) United States Patent
Mueller

(10) Patent No.: US 9,089,440 B2
(45) Date of Patent: Jul. 28, 2015

(54) KNOCKOUT TOOL FOR MINIMALLY INVASIVE PROSTHESIS REVISION

(71) Applicant: Erich Johann Mueller, Kleinwallstadt (DE)

(72) Inventor: Erich Johann Mueller, Kleinwallstadt (DE)

( * ) Notice: Subject to any disclaimer, the term of this patent is extended or adjusted under 35 U.S.C. 154(b) by 88 days.

(21) Appl. No.: 13/777,566

(22) Filed: Feb. 26, 2013

(65) Prior Publication Data

US 2014/0207123 A1    Jul. 24, 2014

(30) Foreign Application Priority Data

Jan. 22, 2013   (DE) .......................... 10 2013 200 924

(51) Int. Cl.
*A61F 2/46* (2006.01)
*A61B 17/58* (2006.01)
*A61F 2/30* (2006.01)

(52) U.S. Cl.
CPC .............. *A61F 2/4603* (2013.01); *A61F 2/461* (2013.01); *A61F 2/4607* (2013.01); *A61F 2/4609* (2013.01); *A61F 2002/30565* (2013.01); *A61F 2002/4619* (2013.01); *A61F 2002/4622* (2013.01); *A61F 2002/4628* (2013.01)

(58) Field of Classification Search
CPC ....... A61F 2/46; A61F 2/4607; A61F 2/4609; A61F 2/461; A61F 2/4603; A61F 2/4612; A61F 2002/4622; B25B 7/06; B25B 7/12; B25B 5/04; B25B 5/12
USPC ................. 606/86 A, 86 B, 86 R, 91, 99, 100
See application file for complete search history.

(56) References Cited

U.S. PATENT DOCUMENTS

| | | | | |
|---|---|---|---|---|
| 5,122,130 A | * | 6/1992 | Keller | ........................ 606/86 A |
| 5,169,399 A | * | 12/1992 | Ryland et al. | ................... 606/91 |
| 5,190,550 A | * | 3/1993 | Miller et al. | .................... 606/85 |
| 5,324,293 A | * | 6/1994 | Rehmann | ........................ 606/85 |
| 5,417,693 A | | 5/1995 | Sowden et al. | |
| 5,443,471 A | * | 8/1995 | Swajger | ......................... 606/99 |
| 5,534,006 A | * | 7/1996 | Szabo et al. | ................. 606/100 |

(Continued)

FOREIGN PATENT DOCUMENTS

| | | |
|---|---|---|
| DE | 10013331 A1 | 9/2001 |
| DE | 102006042141 B3 | 4/2008 |

(Continued)

OTHER PUBLICATIONS

European Office Action dated Apr. 3, 2014.

(Continued)

*Primary Examiner* — Christian Sevilla
*Assistant Examiner* — Eric S Gibson
(74) *Attorney, Agent, or Firm* — Baker & Hostetler LLP

(57) ABSTRACT

A tool head for a surgical tool for knockout and/or insertion of prostheses is disclosed, comprising a tool body (10, 11, 12) having at least two clamping jaws (14, 14*a*, 14*b*, 14*c*, 15, 15*a*, 15*b*, 41) for clamping a prosthetic part, wherein at least one of the clamping jaws is mounted to be movable in relation to the tool body (10, 11, 12); wherein at least one of the movable clamping jaws has at least one pressure area (16), which is arranged so that applying a pressure to the pressure area (16) of the at least one clamping jaw causes a movement of the clamping jaws (14, 14*a*, 14*b*, 14*c*, 15, 15*a*, 15*b*, 41) toward one another or away from one another, to thereby clamp the prosthetic part between the holding areas of the clamping jaws.

7 Claims, 9 Drawing Sheets

(56) References Cited

U.S. PATENT DOCUMENTS

| | | | |
|---|---|---|---|
| 5,540,697 A * | 7/1996 | Rehmann et al. | 606/91 |
| 5,582,084 A * | 12/1996 | Sarmiento | 81/345 |
| 5,951,564 A * | 9/1999 | Schroder et al. | 606/100 |
| 6,322,564 B1 | 11/2001 | Surma | |
| 7,879,042 B2 * | 2/2011 | Long et al. | 606/99 |
| 7,998,144 B2 * | 8/2011 | Schumacher et al. | 606/99 |
| 8,114,092 B2 * | 2/2012 | Altarac et al. | 606/99 |
| 8,157,808 B2 * | 4/2012 | Keller | 606/99 |
| 8,231,633 B2 * | 7/2012 | Lim et al. | 606/99 |
| 8,262,667 B1 | 9/2012 | Silver et al. | |
| 8,277,460 B2 * | 10/2012 | Mcmillan et al. | 606/99 |
| 8,282,649 B2 * | 10/2012 | Long et al. | 606/99 |
| 8,298,241 B2 * | 10/2012 | Arnhold | 606/99 |
| 8,486,084 B2 * | 7/2013 | Huene | 606/100 |
| 8,523,874 B2 * | 9/2013 | Bonvallet et al. | 606/99 |
| 8,603,100 B2 * | 12/2013 | Muller | 606/100 |
| 8,608,752 B2 * | 12/2013 | Ralph et al. | 606/99 |
| 8,657,833 B2 * | 2/2014 | Burgi et al. | 606/99 |
| 8,657,834 B2 * | 2/2014 | Burgi | 606/99 |
| 8,702,719 B2 * | 4/2014 | Refai et al. | 606/99 |
| 8,753,406 B2 * | 6/2014 | Lozier et al. | 623/23.48 |
| 2002/0072752 A1 * | 6/2002 | Zucherman et al. | 606/99 |
| 2003/0225416 A1 * | 12/2003 | Bonvallet et al. | 606/105 |
| 2004/0158257 A1 * | 8/2004 | Bonati et al. | 606/99 |
| 2005/0209597 A1 * | 9/2005 | Long et al. | 606/86 |
| 2006/0178673 A1 * | 8/2006 | Curran | 606/100 |
| 2007/0088438 A1 * | 4/2007 | Cauthen, III et al. | 623/17.11 |
| 2007/0123903 A1 * | 5/2007 | Raymond et al. | 606/99 |
| 2007/0123907 A1 * | 5/2007 | Weber | 606/99 |
| 2008/0077241 A1 * | 3/2008 | Nguyen | 623/17.11 |
| 2008/0154277 A1 * | 6/2008 | Machalk et al. | 606/99 |
| 2008/0161821 A1 * | 7/2008 | Heinz | 606/99 |
| 2008/0208202 A1 * | 8/2008 | Williams | 606/100 |
| 2008/0255574 A1 * | 10/2008 | Dye | 606/99 |
| 2008/0262503 A1 * | 10/2008 | Muller | 606/99 |
| 2009/0112217 A1 * | 4/2009 | Hester | 606/99 |
| 2009/0138095 A1 * | 5/2009 | Giordano | 623/23.72 |
| 2009/0143785 A1 * | 6/2009 | Chang et al. | 606/99 |
| 2009/0292361 A1 * | 11/2009 | Lopez | 623/17.15 |
| 2009/0306672 A1 * | 12/2009 | Reindel et al. | 606/90 |
| 2010/0030223 A1 * | 2/2010 | Keller | 606/99 |
| 2010/0123325 A1 * | 5/2010 | Maffeis | 294/88 |
| 2012/0143204 A1 * | 6/2012 | Blaylock et al. | 606/99 |
| 2014/0163561 A1 * | 6/2014 | Sharp et al. | 606/84 |
| 2014/0207123 A1 * | 7/2014 | Mueller | 606/1 |

FOREIGN PATENT DOCUMENTS

| | | |
|---|---|---|
| EP | 0333990 A2 | 9/1989 |
| FR | 2742334 A1 | 6/1997 |
| WO | 9325164 A1 | 12/1993 |
| WO | 2007062103 A1 | 5/2007 |
| WO | 2007068219 A1 | 6/2007 |
| WO | 2008028451 A1 | 3/2008 |

OTHER PUBLICATIONS

German Office Action dated Oct. 4, 2013.

* cited by examiner

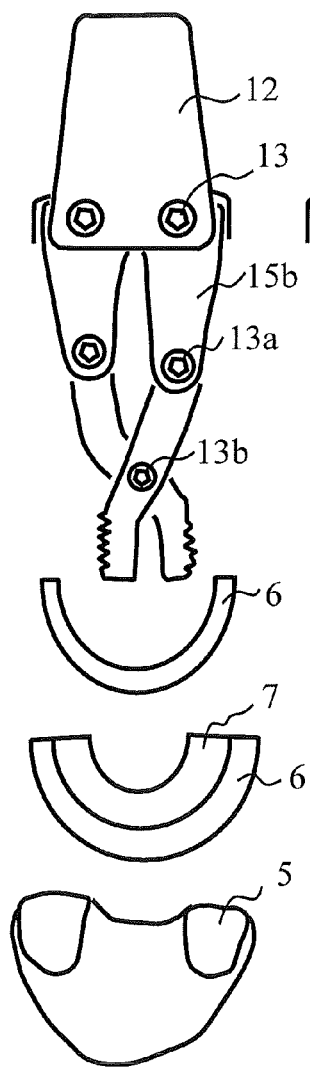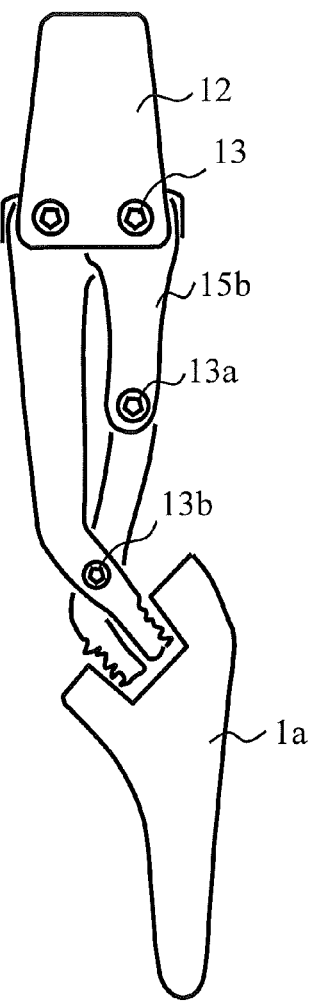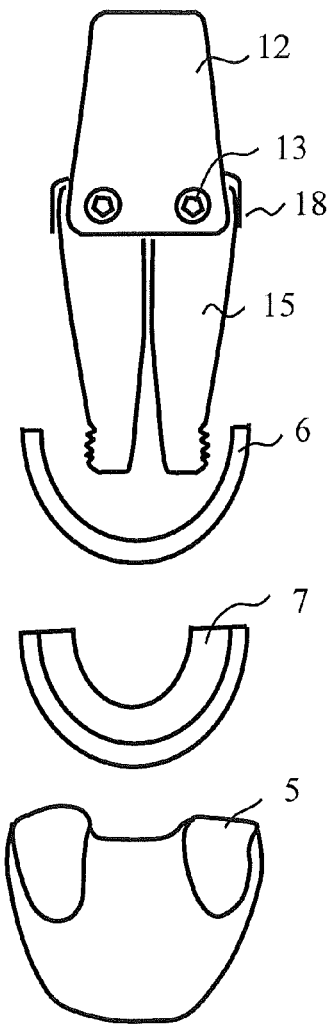

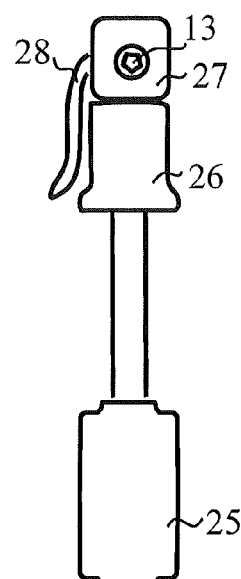
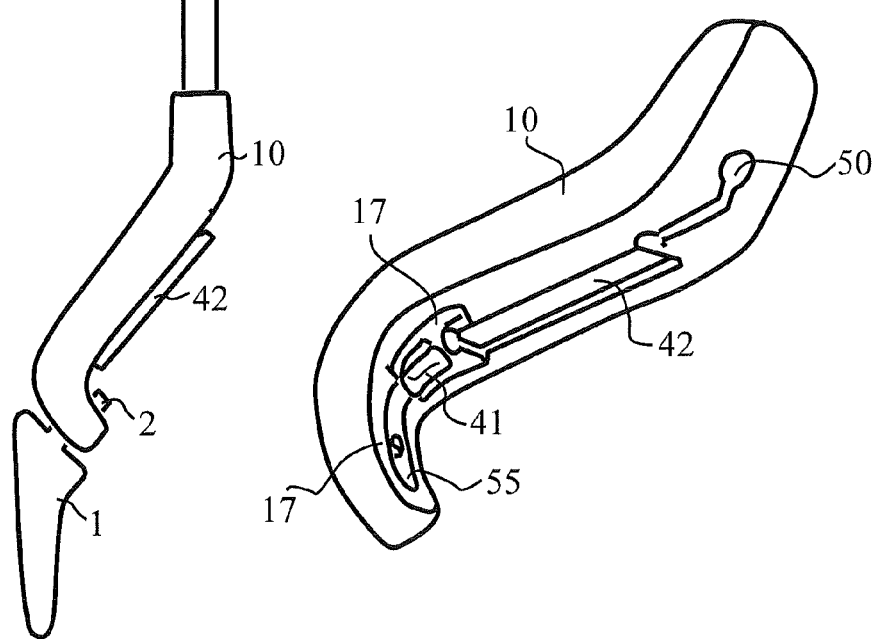
Fig. 12a
Fig. 12b

KNOCKOUT TOOL FOR MINIMALLY INVASIVE PROSTHESIS REVISION

REFERENCE TO RELATED APPLICATIONS

This application claims priority of German patent application no. DE 10 2013 200 924.0, filed on Jan. 22, 2013, the disclosures of which are incorporated by reference in its entirety.

FIELD OF THE INVENTION

The invention relates to surgical tools for insertion and knockout of joint prostheses.

BACKGROUND OF THE INVENTION

For many decades artificial joints and joint prostheses have been used surgically, for example, hip joint prostheses, shoulder prostheses or knee prostheses. The hip joint prosthesis is thus the most commonly performed joint replacement surgery. In Germany alone, approx. 200,000 hip joint endoprostheses are implanted each year. Each year, more than 175,000 people have surgery on their knees due to wear on the joint. However, the stability of these prostheses is limited and therefore they must be replaced after a certain amount of time, in particular due to aseptic loosening of the implants. In the case of a hip joint prosthesis, the service life today is 10-15 years, for example. The incidence of revision surgery in the first ten years after implantation is 10%.

Nevertheless, even a loosened prosthesis or prosthetic part will usually still be very securely attached to and enmeshed with the respective bone structures. Therefore there are still problems in removing a prosthesis from the body without causing sequelae to the surrounding bone bed and/or the patient's other tissues. Conditions are also similar when introducing new prostheses. Furthermore, it is advantageous for the patient to perform the procedure in the manner that conserves as much of the surrounding tissue as possible, so that minimally invasive surgical procedures (MIS) with the smallest possible opening of or injury to the skin and surrounding tissue would be desirable and in the meantime have become quite conventional. Positive effects include the preservation of muscle attachments, preservation of muscle functions, reduced postoperative pain symptoms and faster rehabilitation of the patient. However, this also makes high new demands of the instruments used in minimally invasive insertion and removal of prostheses.

The forces in knocking out a prosthesis must thus be high enough but at the same time they must be transferred in a very targeted manner so that they act only on the shaft/neck of the prosthesis. A very high momentum is necessary to release the bond between the prosthesis and the bony tissue before the energy can be transferred to the bone. This requires an axial transfer force with accurate positioning of the tools as much as possible.

Previous knockout tools can often be used only for one type of prosthesis and in some cases only for prostheses of a specific design and/or a certain manufacturer. Furthermore, the positioning and fixation of the tool are not simple to achieve, as explained above.

SUMMARY OF THE INVENTION

The object of the present invention is therefore to provide a surgical tool for knockout and/or insertion of joint prostheses which will allow gentle removal of the prosthetic parts for different joints in minimally invasive procedures.

This object is achieved by a tool head and a tool according to the accompanying claims.

A tool according to the present invention comprises essentially two parts, a tool head which serves to knock out the prosthesis and an operating part which serves to operate the tool head. In this way, all the steps for operation of the tool take place outside of the operating field, which permits improved operability for the surgeon, among other things, but also allows minimally invasive procedures in particular because there need not be any protruding operating elements such as screws or levers on the tool head. A prosthesis or a prosthetic part can easily be clamped and secured reliably by means of clamping jaws on the tool head, which are operated by remote operating elements on the operating part and are not operated directly on the tool head. After clamping the prosthetic part, a targeted axial momentum for knockout or insertion of the prosthesis can then be applied by means of the operating part. The convenient positioning permits a gentle knockout with minimal damage to the surrounding tissue. Furthermore, the tool may have a modular design, so that any operating part can be combined with a wide variety of tool heads. This yields a versatile knockout tool, which can be adapted optimally to the specific conditions of each prosthesis and the required forces.

The invention comprises a tool head for a surgical tool for knockout and/or insertion of prostheses, comprising a tool body 10, 11, 12 having at least two clamping jaws 14, 14a, 14b, 14c, 15, 15a, 15b, 41 for clamping a prosthetic part, so that at least one of the clamping jaws is mounted movably in relation to the tool body 10, 11, 12; wherein at least one of the movable clamping jaws has at least one pressure area 16, which is arranged so that a pressure exerted on the pressure area 16 of the at least one clamping jaw produces a movement of the clamping jaws 14, 14a, 14b, 14c, 15, 15a, 15b, 41 toward or away from one another, to thereby clamp the prosthetic part between the holding areas of the clamping jaws. With such a tool head, the pressure exerted by means of a corresponding operating part can also be applied indirectly and therefore at a desired distance outside of the operating field, which permits minimally invasive operations.

According to an exemplary embodiment, the clamping jaws are designed as pliers with two clamping jaws 14, 14a, 14b, 14c, 15, 15a, 15b, which are pivotably mounted on the tool body 12. These clamping jaws may be arranged either in a straight line or crossed. If they are crossed, the at least two clamping jaws 14c, 15a, 15b may be connected at their point of intersection by a pin joint 13b.

According to another embodiment, at least one of the clamping jaws 14, 14a, 14b, 15a may be angled at the side in relation to the axis of the tool to achieve an advantageous force vector for example.

Depending on the embodiment, the clamping jaws, which are designed like pliers, may be arranged in such a way that they move away from one another toward the outside or toward one another on the inside when a pressure is applied to the pressure area.

In special embodiments, at least one of the clamping jaws, designed like pliers, may comprise multiple sections, each being pivotably connected to one another by a pin joint 13a.

In an alternative embodiment of the invention, the tool body 10, 11 has a sliding rail or guide 50 in which a movable clamping jaw 41 is displaceably mounted such that a second clamping jaw is formed by an end area of the tool body 10, 11. The end area of the tool body may have an opening 55, 55a to receive a prosthetic part such that the movable clamping jaw 41 is arranged in such a way that it can be moved into the opening. This opening may be a lateral opening or a through-hole so that the opening is of such dimensions that the desired prosthetic part—for example, a prosthetic neck may be accommodated therein.

Furthermore, a control element may be inserted displaceably into the sliding rail of the tool body facing away from the end area and adjacent to the movable clamping jaw, this control element being arranged in such a way that it is capable of exerting a pressure on the movable clamping jaw.

In all the embodiments of the tool head according to the invention, optionally at least one restoring element 18 in the form of a spring, for example, may be provided, returning the clamping jaws 14, 14a, 14b, 14c, 15, 15a, 15b, 41 back to their original position at the end of the application of pressure.

To improve the hold, optionally at least one of the clamping jaws 14, 14a, 14b, 14c, 15, 15a, 15b, 41, optionally in any desired embodiments, may be provided with a profile 17 in a holding area, which is in contact with a prosthetic part that is to be clamped, for example, by being provided with notches or grooves.

The invention also relates to a surgical tool for knockout and/or insertion of prostheses, comprising a tool head as described above and an operating part such that the operating part comprises a guide housing 20, 29, 30 with an axial recess, which is open at least in the direction of the tool head; an adjusting rod 43, 43a which is mounted to be axially displaceable in the guide housing 20, 29, 30; and operating element 28 and a striker mechanism 30a, 29a, 25, 26 which is equipped to receive or to apply the momentum applied to the operating part and to transfer it to the prosthesis by way of the tool; wherein the tool body 10, 11, 12 of the tool head is attached to the guide housing 20, 29, 30 of the operating part; characterized in that the operating element 28 is arranged in such a way that operation of the operating element 28 produces a movement of the adjusting rod 43, 43a in the direction of the tool head such that the adjusting rod is arranged so that it exerts a pressure on the pressure area 16 of the at least one movable clamping jaw 14, 14a, 14b, 14c, 15, 15a, 15b, 41 when operated.

The striker mechanism may comprise, for example, a striker plate 29a for receiving a mechanical impact on the end of the operating part facing away from the tool head; or a slide hammer 25, which is movably supported on the guide housing 20, and a stop 26 for the slide hammer on one or both ends of the guide housing; or a pneumatic adapter for connecting a pneumatic tool. The operating element 28 may comprise an eccentric lever, for example.

The tool head is preferably detachably attached by a thread to the operating part.

BRIEF DESCRIPTION OF THE DRAWINGS

The invention will be described in greater detail below with reference to the figures, wherein

FIGS. 5, 6, 7, 8, 9 and 10 each show different tool heads as examples with the function of pliers for various areas of use;

FIG. 12a shows another embodiment of a tool with an operating point, where FIG. 12b shows only a corresponding tool head alone in greater detail.

DETAILED DESCRIPTION OF THE INVENTION

Figure 1:
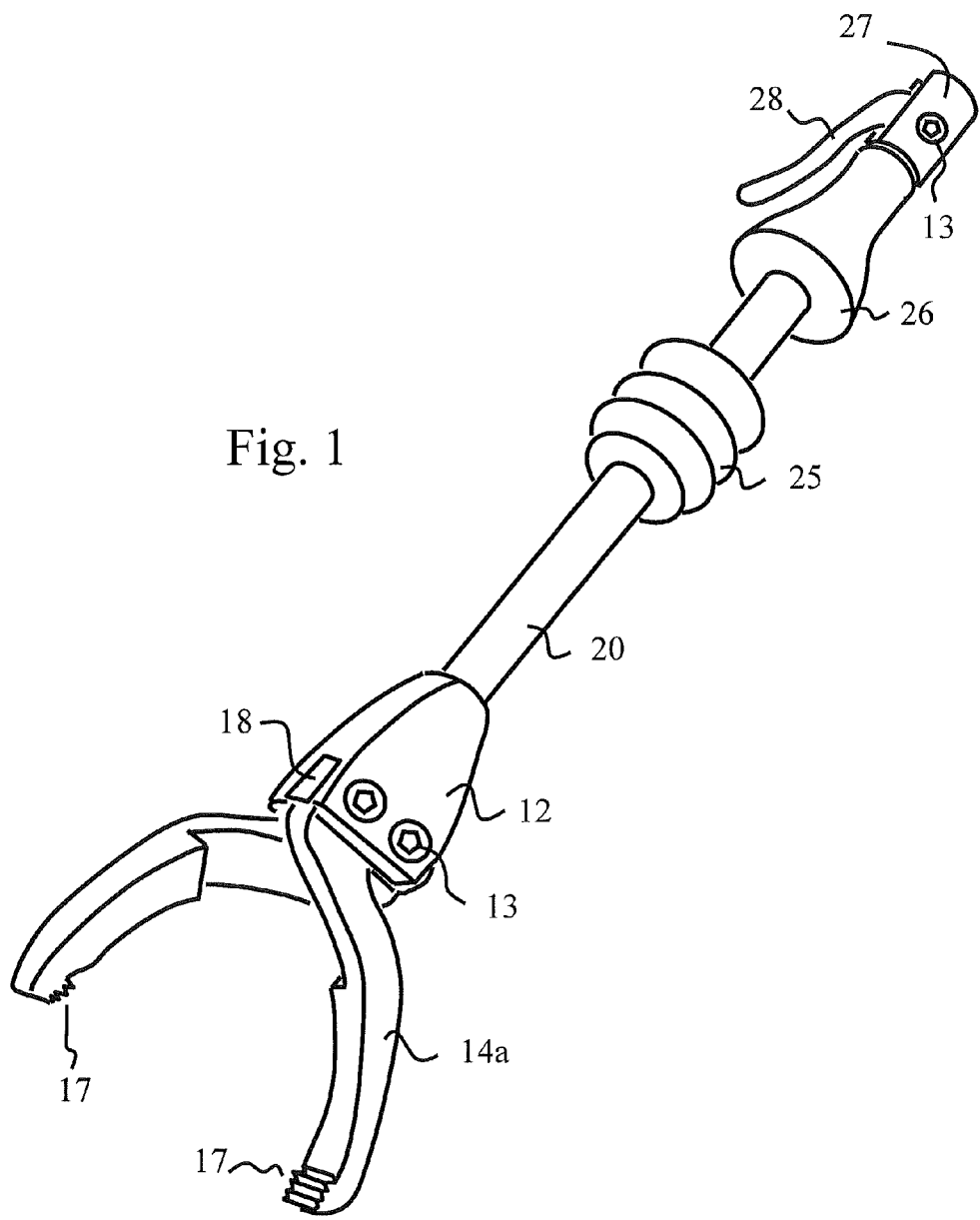
FIG. 1 shows a perspective view of a tool according to the invention with a tool head and an operating part according to the slide hammer principle.

FIG. 1 shows one possible embodiment of a tool according to the invention. The tool head comprises a tool body 12 and two clamping jaws 14a which are designed like pliers and are both movably attached to the tool body 12 by means of pins or bolts 13 in this exemplary embodiment. During use, the clamping jaws are placed against the prosthesis and moved toward one another by means of the operating part as described below, so that the prosthesis can be gripped at least in the holding area 17 and clamped there. In the example shown here, the holding area 17 also has notches or grooves which ensure an improved engagement with the prosthetic part to be clamped. Instead of the notches, other types of profiling such as peaks or grooving may be provided in at least one of the holding areas or, if the contact pressure is sufficient even in the case of a smooth tool, they may be omitted completely. The clamping jaws 14a are arranged in a crossed pattern and have a curved shape. The clamping jaws will of course have dimensions such that they are adapted to the diameter and the usable holding services of the prosthetic part to be clamped, for example, a prosthesis neck. A plate spring 18 may be applied to one or both clamping jaws 14a in the area of the tool body 12, so that when there is a reduction in the adjusting force on the clamping jaws, the same will return to the original position to remove the tool from the prosthesis.

The operating point of the tool is attached to the tool body 12. In this example, the operating part comprises a guide rod 20, a hammer part 25, which is slidingly supported on this rod, a gripping handle 26 and a control element 28 in the form of an eccentric lever. The eccentric lever is connected to the gripping handle by means of a hinge or pin 13. An adjusting rod, which runs inside the guide rod 20, is not visible here but will be described in greater detail in conjunction with FIG. 2. The adjusting device consisting of the adjusting rod and the adjusting element and/or lever permits operation of the clamping jaws, which are designed like pliers, so that in operation of the lever 28, the two clamping jaws 14a are moved toward one another and the tool is clamped. The slide hammer then makes is possible to transfer the momentum to the clamped prosthetic part in that the hammer part is moved upward or downward slidingly as far as a stop on the guide rod 20. In this way, the prosthetic part can be secured between the clamping jaws and removed by means of a slide hammer.

Figure 2:
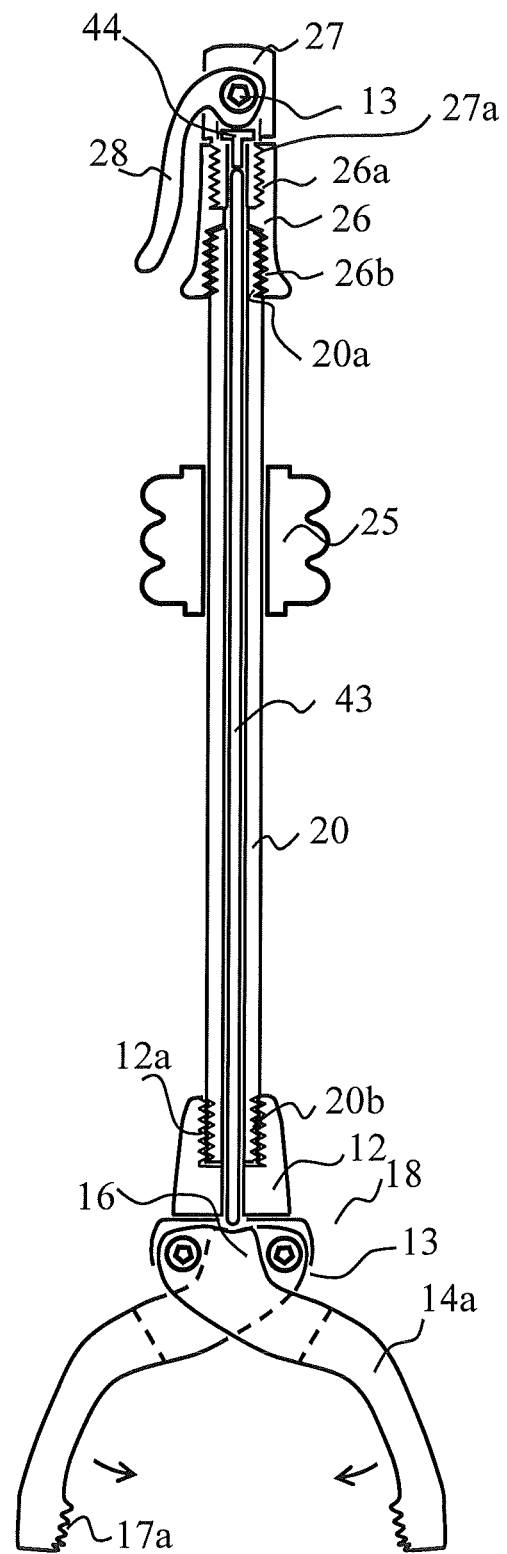
FIG. 2 shows a cross section through a tool like that shown in FIG. 1.

FIG. 2 shows the example of the tool from FIG. 1 in cross section where the functioning of the control element is obvious. This again shows the tool head with the tool body 12 to which the two clamping jaws 14a with the notched holding areas 17 are movably attached with the pins 13. The tool head is detachably connected by means of the thread 12a and/or 20b to the guide rod 20 on which the hammer piece 25 can slide. The guide rod has a bushing on the inside in which the adjusting rod 43 runs. The gripping handle 26 of the slide hammer is secured by means of the thread 26b and/or 20a on the end of the guide rod facing away from the tool head. In addition, the clamping part 27 to which the eccentric lever 28 is movably attached as an adjusting element by means of a pin 13 is also mounted by means of a thread. Between the lever 28 and the adjusting rod 43 a pressure piece 44 ensures the transfer of force. In another embodiment, however, the eccentric lever 28 could act directly on the adjusting rod 43.

The adjusting rod 43 and the clamping jaws 14*a* are arranged so that a movement of the adjusting rod 43 downward in the direction of the tool head exerts a pressure on a pressure area or pressure wing 16 of the clamping jaws, such that the pressure area is arranged directly beneath the adjusting rod. The pressure exerted downward via the adjusting rod 43 in this embodiment causes the clamping jaws and thus their holding areas to be moved toward one another because of the curved and crossed design of the clamping jaws 14*a*. Thus when the lever 28 is put under tension, this forces the adjusting rod in the direction of the tool head and presses the clamping jaws toward one another, so that a prosthetic part situated in between them is thereby clamped. After a prosthetic part has been secured via the clamping device in this way, the slide hammer is used in the usual way to knock out the prosthesis by deflecting the hammer part upward against the stop of the handle part 26. FIG. 2 also shows the plate springs 18 at the side in the area of the fastening of the clamping jaws, which open the clamping jaw design as soon as the pressure on the pressure area has been released again.

Figures 3A, 3B:
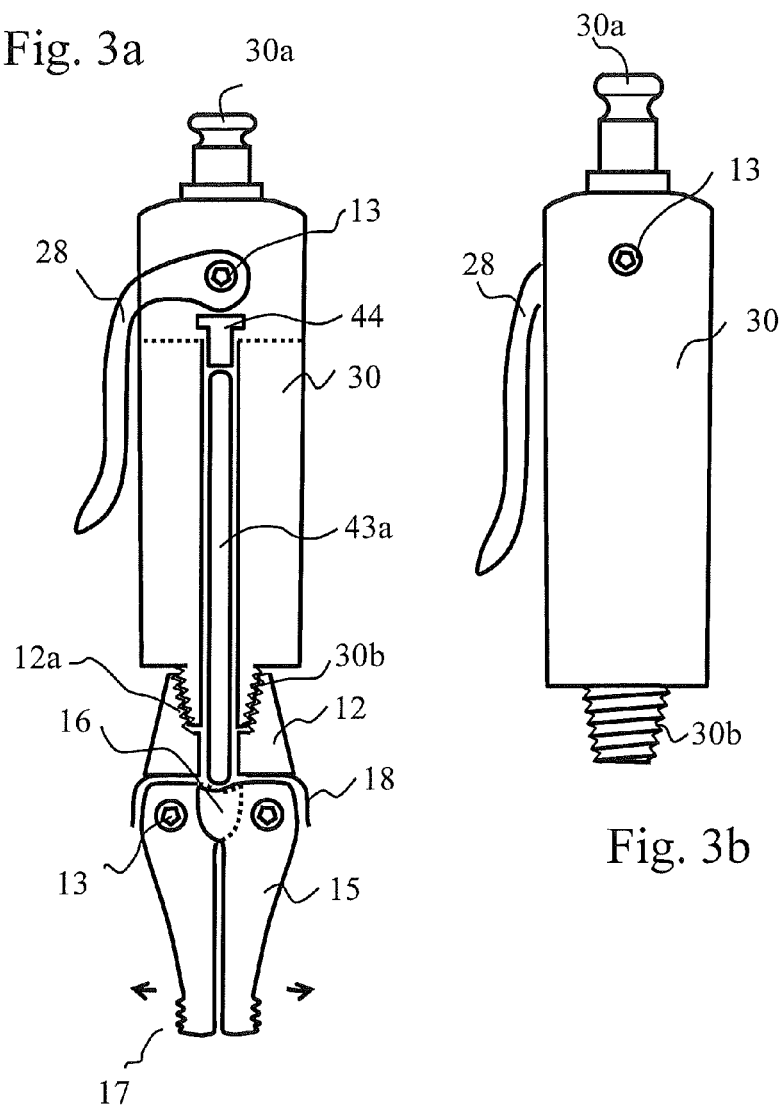
FIG. 3a shows a cross section through another embodiment of a tool according to the invention having an operating part with a pneumatic adapter.
FIG. 3b shows the same operating part alone and without the tool head.

FIG. 3*a* shows another exemplary embodiment in cross section. In this case the tool head is also equipped with clamping jaws 15, which are designed like pliers, although the legs of the clamping jaws here have an approximately linear design and do not intersect. Pressure on the pressure area 16, as described above for FIG. 2, therefore ensures a movement of the two clamping jaws 15 away from one another as indicated by the arrows. For this reason, the notched holding areas 17 are also arranged on the outside of the clamping jaws in this case.

Instead of the slide hammer device with the guide rod, this embodiment shows a clamping handle 30 with a pneumatic adapter 30*a*, so that the striker momentum or a pneumatic tensile force can be applied by way of a connected pneumatic tool. FIG. 3*b* shows this clamping handle with the pneumatic connection without the attached tool head in a view from above. Otherwise the handle 30 is designed like that in the preceding embodiment of FIG. 2. An interior recess which is open in the direction of the tool head is provided in this handle 30. An adjusting rod 43*a* runs in this recess and can be moved in the direction of the tool head by operation of the lever 28 on the upper end and can exert a pressure on the pressure area 16 of the clamping jaws 15 in this area, causing them to move outward as a result. Optionally there is again a pressure piece 44 for the transfer of force between the adjusting rod 43*a* and lever 28. The handle 30 may of course also be designed as a rod or in another suitable form as in FIG. 2.

According to the invention the tool head may be detachably connected to the operating part, as shown in FIGS. 2 and 3, e.g., by means of a thread. In the figures shown here, an inside thread (11*a*, 12*a*) is provided on the tool head and an outside thread (12*b*, 20*b*, 29*b*, 30*b*) is provided on the operating part. Other thread combinations may of course also be used. Likewise, other fastening options are also conceivable, for example, plug connections, which are optionally additionally secured by screws or clamps. However, a special tool for a certain intended purpose could also have a one-piece connection or at least a non-releasable connection between the tool head and the operating part.

Figure 4A:
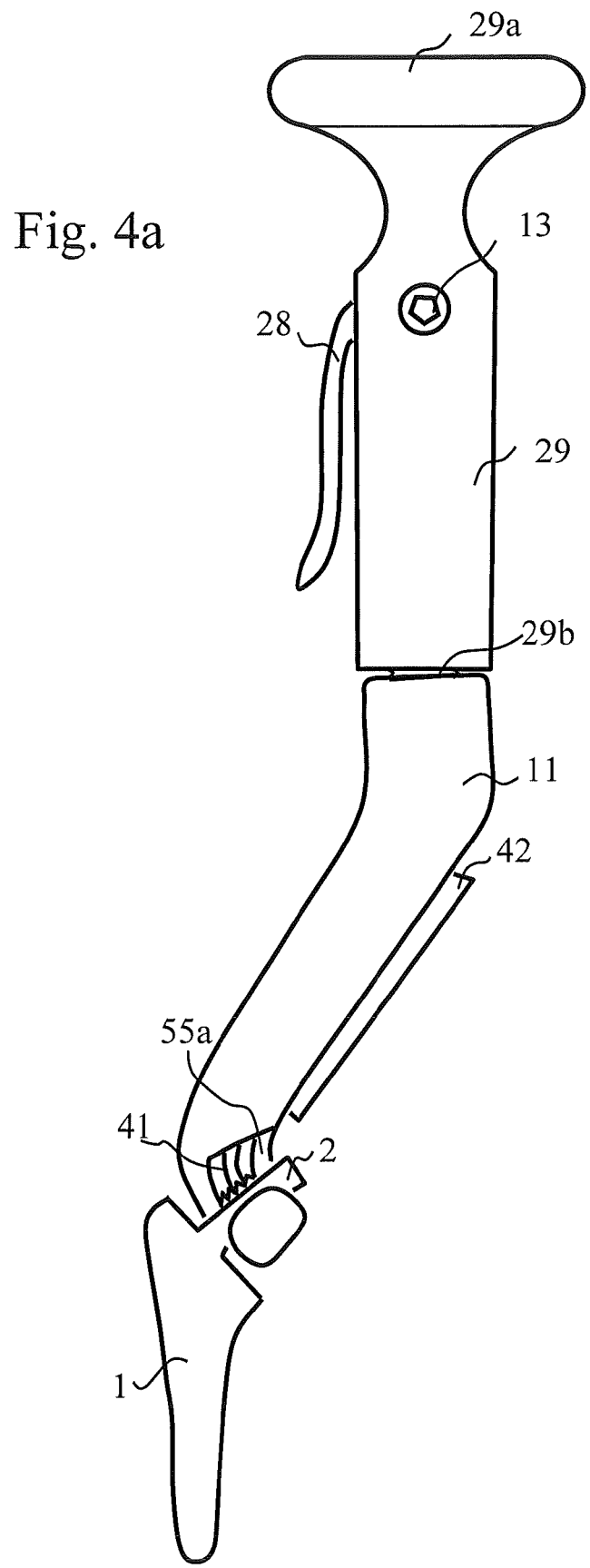
FIG. 4a shows an embodiment of a tool with a stop plate and a tool head with a hip joint prosthesis, where
Figure 4B:
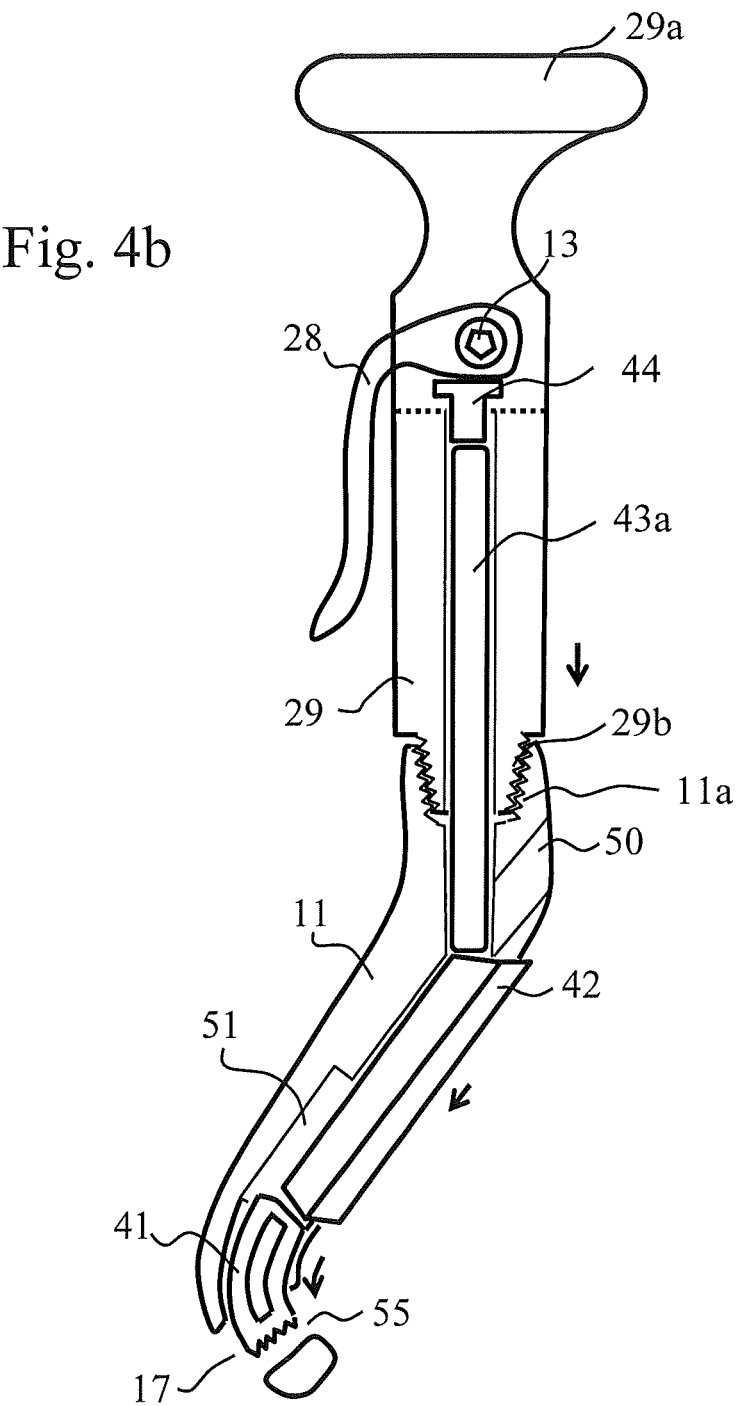
FIG. 4b shows a corresponding tool in cross section.

FIG. 4*a* shows a view from above of another embodiment of the invention; FIG. 4*b* shows the same tool composition in cross section. The handle 29 does not have a pneumatic adapter as shown in FIG. 3 but instead has a striker plate 29*a* on the end facing away from the tool head. The other parts, namely the lever 28 with the fastening pin 13, the handle 29 with the recess for the adjusting rod 43*a* and the functioning of the operating part are all consistent with those in the preceding embodiment. A hammer strike or momentum created in some other way may be applied to the striker plate, so that the momentum can be transferred to the clamped prosthesis.

However the tool head shown in FIG. 4 is not equipped with clamping jaws designed like pliers, but instead with a movable clamping jaw 41, which is pressed against a stationary clamping jaw, which is designed as a curved extension of the tool body 11. The tool body 11 is curved starting from the connecting area between the operating part and the tool head and has a guide 50 for another control element 42 in the tool body, which is displaceably mounted in this guide. Following that, the movable clamping jaw in the form of an insertable clamping member is displaceably introduced into an opening 51 in the tool body. During use, the adjusting rod 43*a* exerts pressure on the control element 42 during operation, and this in turn reflects the pressure on the clamping jaw 41 which is thus forced in the direction of the end area of the tool body so that the end area thus forms the second stationary clamping jaw. The tool body is open at the side 55*a* in this area to receive a prosthetic part, for example, the prosthesis neck of a hip prosthesis, as shown in FIG. 4*a*. The end of the clamping jaw 41 may here again be provided with notches 17 for a more secure hold on the prosthetic part. As soon as the prosthetic part has been accommodated in the opening 55*a* (which is exposed as long as the clamping device has not been operated), the clamping jaw 41 can be forced in the direction of the opening by the operation of the lever on the operating part to thereby clamp the prosthetic part between the holding area of the clamping jaw and the end area of the tool body.

All the operating parts shown above can be combined in any desired way with the tool heads of the previous figures as well as the following figures, i.e., may be combined with the slide hammer operating parts as well as with the striker plate handle or the pneumatic handle. Likewise other operating parts not described here may also conceivably be used with such tool heads. The fastening onto operating parts is accomplished by means of a thread on both ends or some other stable fastening mechanisms, as is also the case in the preceding examples. Likewise the tool heads of the following figures may be fixedly connected to a suitable operating part. Of course tool heads and tools of this type can be used not only for knockout of endoprostheses but also, for example, for knocking out screws that have broken off.

Figures 5, 6, 7:
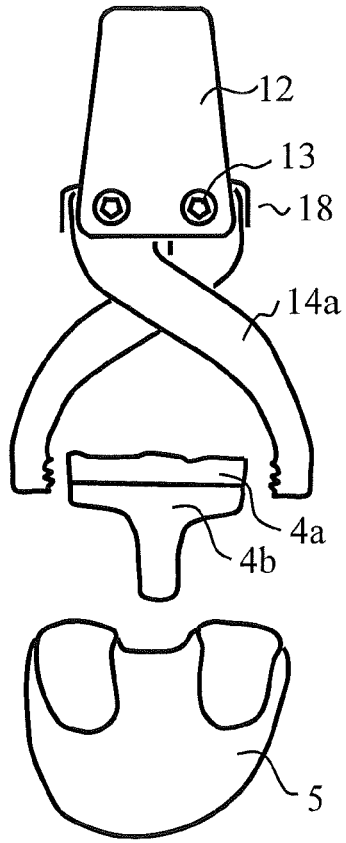

FIG. 5 shows an exemplary tool head according to the present invention without an attached operating part. The clamping jaws 14*c* in this example are designed like pliers and consist of multiple moving sections which are connected to one another by means of pins 13, 13*a*, 13*b*. In this example as well as in the following examples, the pressure areas are not shown but instead are also applied centrally between the fastening pins 13 as in the preceding examples so that pressure on the pressure area will result in a movement of the clamping jaws. In FIG. 5 the clamping jaws comprise two plier-like parts that are crossed like scissors, with the holding areas having notches for holding the prosthetic part 3 provided on the angled ends thereof. These two parts are connected with a pin 13*b* at the centre so that they can rotate. Two additional plier sections and/or jaw sections are fastened between these end parts and the tool body using pins 13*a* and 13 so that they intersect and when a pressure is applied to a pressure area (not shown) between the fastening pins 13, the two clamping jaws move toward one another and the hold can be further increased by mechanical tension on the plier system. In the example shown here, the head 3 of a modular femoral prosthesis 1 is shown as the prosthetic part to be clamped; as an alternative, the neck 2a of a modular prosthesis, a screw 9 or a medullary nail 8 may be used.

FIG. 6 shows another plier-like example of a tool head in which two crossed clamping jaws 14b having a concave curvature or attached to the tool body 12 by means of pins 13. Here again, the end areas of the clamping jaws are moved toward one another to thereby secure the head 3 of a femoral prosthesis 1 as an example, or alternatively, to secure a screw 9, a nail 8 or the neck of a prosthesis.

The pliers-like formation of the clamping jaws 14a in FIG. 7 resembles the embodiment illustrated in FIG. 6 in that the curvature and/or the angles of the clamping jaws 14a are different and therefore are adapted to the dimensions of the prosthetic part to be gripped, which in this example represents the tibial component 4a, 4b of a knee prosthesis. It is also apparent that the holding areas in FIG. 6 are designed to be rounded to thereby be adapted optimally to the round prosthesis head 3 while here in Example 7 straight holding areas are provided for the maximal acting force.

FIG. 8 shows another exemplary tool head with pliers-like clamping jaws 15b, each of which consists of two sections. The lower sections of the clamping jaws are crossed and are connected by means of a hinge pin 13b while the upper sections of the pliers which are connected to the lower sections are not crossed and are attached by means of pins 13a and 13 between the lower sections and the tool body 12. Therefore, when a pressure is exerted on the pressure area (not shown here), the result is a movement of the clamping jaws outward. In this way it is possible to intervene in a cavity, for example, as shown in an inlay 7 or a socket 6 of a hip joint prosthesis or also in the curvature of the femoral component 5 of a knee prosthesis. The notches in the holding area are consequently arranged on the outside of the clamping jaws.

FIG. 9 shows another exemplary tool head whose clamping jaws 15a move outward under pressure and therefore can engage in a cavity and/or a recess in a prosthetic part 1a. The areas of the clamping jaw beneath the connecting hinge pin 13b here are bent to the side to allow optimal engagement in the recess in the shaft 1a of a modular hip joint prosthesis for example. A clamping jaw is designed in one piece and is connected to the tool body 12 directly above a pin 13; the second clamping jaw comprises two sections which are connected to one another by a pin 13a.

This design is the result of the lateral bend in the holding areas.

Finally, FIG. 10 discloses a simpler embodiment of a tool head whose clamping jaws move outward. The clamping jaws 15 are designed to be essentially straight and are connected directly to the tool body 12 without being crossed. Such an embodiment is also suitable, for example, for fixation of a socket 6 or an inlay 7 of a hip joint prosthesis.

It will be pointed out again here that in each of the tool heads shown here as examples in FIGS. 5 through 10, there is an area over which a movement of the adjusting rod 43, 43a can be transferred to the clamping jaws in a connected operating part. This can be accomplished, for example, by a pressure area and/or pressure wings by means of a clamping jaw, as shown in cross section in FIGS. 2 and 3.

FIG. 11 shows again a tool having an operating part and a tool head. The operating part corresponds to a slide hammer part as described in detail in conjunction with FIGS. 1 and 2. The tool head comprises two clamping jaws 14 that are movable in the manner of pliers but are angled to the side with respect to the perpendicular tool axis immediately after the fastening of the pin 13 on the tool body 12. In this way the clamping jaws can move toward one another when pressure is applied to the pressure area (not shown here) and they can clamp the neck 2 of the prosthesis. These bent clamping jaws are preferably advantageously suitable for minimally invasive anterolateral access.

Figure 11:
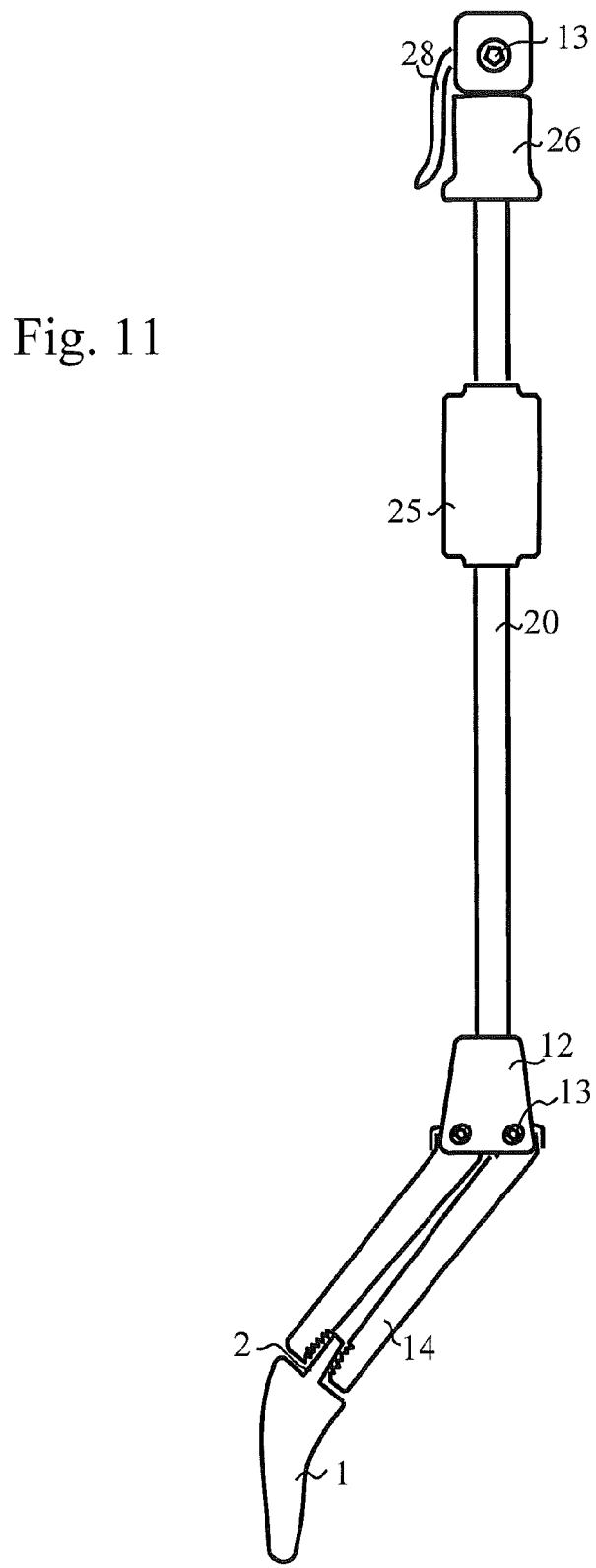
FIG. 11 shows another tool with a slide hammer operating part and a tool head designed like pliers.

FIG. 12a shows another exemplary tool for hip joint prostheses having a slide hammer operating part as illustrated in FIG. 11. The tool body 10 is designed like the tool body 11 described in conjunction with FIG. 4 but the tool body 10 is not open at the side in the end area to receive a prosthetic part but instead is closed and has a through-hole 55 in the end area which can be placed on a prosthesis neck. As in the case of the opened tool body 11, a clamping jaw 41 with notches 17 inserted into the tool body 10 is then pressed against the inserted neck of the prosthesis and thereby clamped between the end area of the tool body, which serves as the second clamping jaw and the movable clamping jaw 41. A more detailed oblique view of this embodiment of a closed tool head 10 with a through-hole 55 can be seen in FIG. 12b. The displaceable control element 42 is again inserted between the clamping jaw 41, which is used as a displaceable clamping member, and the adjusting rod of the operating part, such that the control element slides displaceably in a sliding rail or guide 50 of the tool body 10 and transfers the pressure of the adjusting rod to the clamping jaw 41. Instead of a prosthesis neck of a femoral prosthesis, as shown in FIG. 12a, a similar tool head with a smaller passage diameter could, for example, clamp other prosthetic parts. This tool head is advantageously suitable for a minimally invasive anterolateral access.

It will be clear to those skilled in the art that the different variants of pliers and clamping devices which have been mentioned and presented here in combination with certain joint prosthesis but the areas for use of the embodiments have not been defined specifically. The surgeon will select the tool head most suitable for his specific use. This relates to both the shape of the prosthesis and the presumed required application of force and the angle at which the force must be applied. Those skilled in the art will also be in a position to select or design a pliers-type tool, so that the leg lengths and angles of the clamping jaws can utilize the optimum force ratios, i.e., on the one hand the maximum force for knocking out a prosthesis can be applied and the pressing force of the clamping jaws on the prosthesis is great enough to secure them reliably but on the other hand there is the least possible transfer of force to the bones while the tool remains as easy to operate as possible. The systems of pliers according to the toggle lever principle are also conceivable as the tool head, for example, in which an especially secure fixation of the clamped prosthetic parts may be achieved by pulling. The pliers-type tool head from FIG. 5 corresponds essentially to this principle.

Since the tool has a modular design consisting of the operating part and tool head and the different parts can be dismantled not only at the threads but also easily at the locations that are joined by pins or bolts, this permits simple cleaning of the tools so that all the parts are reusable and also interchangeable. Instead of the pins, other hinge variants may also be used, e.g., screw connections, hinge elements or other approaches known in the field. It is also conceivable in particular to design the pliers-type tool heads, in which the two parts of the pliers are joined by a pin acting as a hinge in the examples, with the pull-through tissue instead, i.e., so that the legs of the pliers and/or the legs of the clamping jaws are not only placed one on top of the other but instead one plier part is passed through an opening in the other plier part.

The situation is similar for the operating element 28 which is depicted as an eccentric lever in the examples. Here again a different element could be used which makes is possible to reliably clamp the clamping jaws by acting on the adjusting rod. It is thus conceivable to clamp the adjusting rod by means of a spring, optionally also in combination with a toothed rod or a geared rack. The operating element is preferably lockable and unlockable so that the tension can be maintained as long as desired.

The plate springs 18, which serve to restore the clamping jaws are helpful but are not necessary for the idea according to the invention. In special embodiments, they may also be omitted or replaced by other restoring elements such as spiral springs or the like. These alternatives may of course be used in all the operating parts shown here and may be combined with all the tool heads of the modular tool. Furthermore it will be understandable to those skilled in the art that the features of individual embodiments can also be combined with those of other examples.

The invention claimed is:

1. A surgical tool for knockout or insertion of a prosthesis, comprising:
    a tool body, comprising: two clamping jaws configured for clamping a prosthetic part, wherein the clamping jaws are mounted to be movable in relation to the tool body;
    wherein at least one of the movable clamping jaws has at least one pressure area which is configured so that exerting a pressure on the pressure area of one clamping jaw causes a movement of the clamping jaws toward one another or away from one another to thereby hold the prosthetic part by engagement with holding areas of the clamping jaws, and
    wherein the clamping jaws are configured as pliers having two clamping jaws which are arranged in a crossed fashion and mounted on the tool body so that they are pivotably attached; and
    an operating part, comprising
        a guide housing having an axial recess which is open at least in a direction of the tool head;
        an adjusting rod mounted to be axially displaceable in the guide housing,
        an operating element, and
        a striker mechanism configured to receive or apply a momentum that is applied to the operating part and to transfer this momentum to the prosthesis by way of the tool;
    wherein the tool body of the tool head is attached to the guide housing of the operating part; and
    the operating element is configured so that operation of the operating element causes a movement of the adjusting rod in the direction of the tool head, such that the adjusting rod is configured so that on actuation it exerts a pressure on the pressure area of at least one movable clamping jaw.

2. The tool according to claim 1, further comprising a knocking device which comprises a striker plate for receiving a mechanical impact on an end of the operating part away from the tool head.

3. The tool according to claim 1, wherein the striker mechanism comprises a slide hammer which is movably mounted on the guide housing and a stop for the slide hammer provided on one or both ends of the guide housing.

4. The tool according to claim 1, wherein the striker mechanism comprises a pneumatic adapter.

5. The tool according to claim 1, wherein the operating element comprises an eccentric lever.

6. The tool according to claim 1, wherein the operating element is indirectly connected to the adjusting rod via an intermediate movable pressure piece.

7. The tool according to claim 1, wherein the tool head is detachably attached to the operating part by a thread.

* * * * *